United States Patent [19]

Topp et al.

[11] Patent Number: 5,663,649
[45] Date of Patent: Sep. 2, 1997

[54] SOIL PENETROMETER

[75] Inventors: Clarke Topp; Bruce Compton, both of Nepean; Keith Wires, Ashton, all of Canada

[73] Assignee: Her Majesty The Queen in right of Canada, as represented by Agriculture and Agri-Food Canada, Ottawa, Canada

[21] Appl. No.: 460,777

[22] Filed: Jun. 2, 1995

[51] Int. Cl.[6] ............................................. G01N 22/00
[52] U.S. Cl. ............................................. 324/643
[58] Field of Search ...................... 73/29.01, 29.02, 73/29.05, 335.02, 335.03, 81, 82, 84; 324/664–670, 643

[56] References Cited

U.S. PATENT DOCUMENTS

| | | |
|---|---|---|
| 3,331,240 | 7/1967 | Nilsson et al. . |
| 3,481,188 | 12/1969 | Mori . |
| 3,712,121 | 1/1973 | Fletcher et al. . |
| 3,797,301 | 3/1974 | Hawes .................. 73/84 |
| 3,906,781 | 9/1975 | Vlasblom ............... 73/84 |
| 3,999,424 | 12/1976 | Pellissier . |
| 4,059,008 | 11/1977 | Torstensson ............ 73/84 |
| 4,061,021 | 12/1977 | Baldwin et al. . |
| 4,726,239 | 2/1988 | Boggess et al. ......... 73/84 |
| 4,929,885 | 5/1990 | Dishman . |
| 5,010,776 | 4/1991 | Lucero et al. . |
| 5,067,346 | 11/1991 | Field . |
| 5,246,862 | 9/1993 | Grey et al. . |
| 5,313,825 | 5/1994 | Webster et al. . |
| 5,316,950 | 5/1994 | Apitz et al. . |
| 5,418,466 | 5/1995 | Watson et al. ......... 324/668 |
| 5,420,517 | 5/1995 | Skaling et al. . |

OTHER PUBLICATIONS

Soil Sci. Soc. Am.J. vol. 56, (1992) pp. 1384–1391, Remote Diode Shorting Improves Measurement of Soil Water by Time Domain Reflectometry, W.R. Hook et al.

International Conference on Measuremeent of Soil and Plant Water Status, vol. 1, Centennial of Utah State University (1987), The Application of Time–Domain Reflectometry (TDR) to Soil Water Content Measurement, G.C. Topp.

Soil Sci. Soc. Am.J. vol. 49, (1985) pp. 19–24, Measurement of Soil Water Content using Time–domain Reflectrometry (TDR): A Field Evaluation, G.C. Topp et al.

Water Resources Research, vol. 16, No. 3, (1980) pp. 574–582, Electromagnetic Determination of Soil Water Content: Measurements in Coaxial Transmission Lines, G.C. Topp et al.

Soil Sci. Can.J. vol. 64, (1984) pp. 313–321, The Measurement of Soil Water Content Using a Portable TDR Hand Probe, G.C. Topp et al.

*Primary Examiner*—Robert Raevis
*Attorney, Agent, or Firm*—Paul Sharpe, McFadden, Fincham

[57] ABSTRACT

A soil penetrometer and method of using this apparatus are disclosed. The method relates to the application of a constant force to a soil penetrometer, the penetrometer capable of detecting soil moisture content by time domain reflectrometry. The use of the constant force eliminates the variable nature of this parameter conventionally encountered in the art, and therefore reduces the complexity of soil parameter calculation.

10 Claims, 4 Drawing Sheets

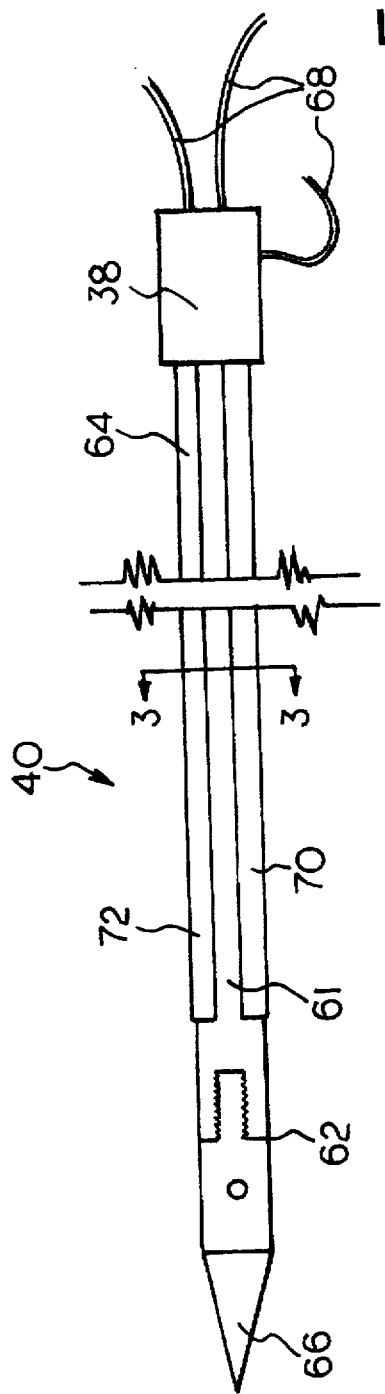
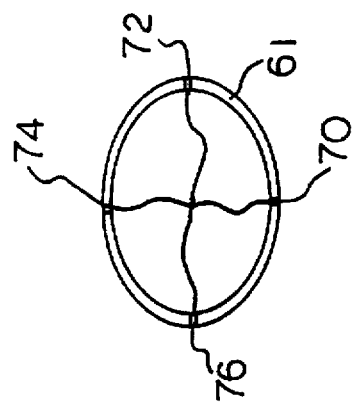

SOIL PENETROMETER

FIELD OF THE INVENTION

The present invention relates to a soil penetrometer and more particularly, the present invention relates to a portable soil penetrometer which has the advantage of detecting soil moisture.

BACKGROUND OF THE INVENTION

Soil cone penetrometer resistance is a good measure of soil strength in relation to root growth, carrying capacity and trafficability. The cone penetrometer can be used as an indicator of the effect of agricultural management practices on soil quality provided the equipment has the capacity to provide detailed and accurate data. Currently, the collection of penetration resistance data requires either the use of heavy mounted equipment or the use of lightweight equipment which requires that the operator manually provide the required force to push the penetrometer into the soil. The accuracy of the data is comprised by the operator's inability to apply a constant force and rate of loading during the penetration.

Assessment of the spacial variability of the penetration resistance requires the equipment to be portable over a wide range of field and crop conditions. The penetration resistance values of soil vary with water content and there is a need to collect water content values to improve the interpretation of the data.

The successful operation of known arrangements relies on the operator controlling and maintaining a constant rate of penetration and applied force during insertion of the penetrometer probe. This is substantially difficult, if not impossible, in soils having layers of varying strength and/or resistance. In addition, the representativeness of the penetrometer measurements is dependent on operator strength and mass which influences one's ability to control both the rate and force parameters. The measurement of soil water content, which is critical for the interpretation of penetration resistance, requires either the instrumentation of an adjacent site for in-situ measurements or the collection of soil samples from each depth increment for laboratory determination of water content. Additional variability is introduced into the data set by this requirement to sample the two neighbouring sites; this serves to compound the statistical analysis by creating added variability within the data set.

In terms of the arrangements which have been proposed in the prior art, U.S. Pat. No. 5,316,950, issued May 31, 1994, to Apitz et al is an example. This reference is reference to a method for quantitative calibration of in-situ optical chemical measurements in soils using soil class and characteristics wherein the probe which optically collects data regarding chemical constituents present within the soil and compares this to known values. This apparatus does not appear to be portable and further, does not make any reference to the use of a constant force apparatus for delivering the probe into the soil or substrate sample to be tested.

Grey et al., in U.S. Pat. No. 5,246,862, issued Sep. 21, 1993 provide a method and apparatus for in-situ detection and determination of soil contaminants wherein the penetrometer provides a reagent carrying tape between the soil and the outer wall of the penetrometer. As the penetrometer is injected into the soil, the tape is pressed against an optical window in the penetrometer and contaminants in the soil react with the reagents and cause a chemical reaction of the tape to occur which is optically detected by the probe.

Similar to U.S. Pat. No. 5,316,950, this reference does not provide for a penetrometer which is capable of controlled and constant force application for the delivery of the probe into the soil and further, the probe does not include means for detecting soil moisture within a substrate sample.

U.S. Pat. No. 4,061,021, issued to Baldwin et al., Dec. 6, 1977, provides a recording soil penetrometer. The penetrometer provides a recording drum which is rotatably mounted to the frame of the apparatus for recording pressure sensitive data thereon. Although the data with respect to the force applied is useful, the apparatus provided for in this reference does not provide a delivery system for the probe which is capable of delivering the probe at a constant force while at the same time providing means for determining the soil moisture content of the soil being tested.

A self-recording portable soil penetrometer is provided in U.S. Pat. No. 3,712,121, issued to Fletcher et al., Jan. 23, 1973. The penetrometer provides the recording drum which is rotatable according to the force applied on the handle of the apparatus and additionally provides a stylus for marking the drum along its height according to the penetration depth of the probe in the soil.

Additional patents which relate to the penetrometer include, for example, U.S. Pat. Nos. 5,313,825, issued to Webster et al. May 24, 1994, U.S. Pat. No. 3,331,240 issued Jul. 18, 1967 to Nilsson et al., U.S. Pat. No. 3,481,118 issued Dec. 2, 1969 to Mori, U.S. Pat. No. 3,999,424 issued Dec. 28, 1976 to Saint-Remy Pellissier, U.S. Pat. No. 5,067,346, issued Nov. 26, 1991 to Field, and U.S. Pat. No. 5,010,776 issued Apr. 30, 1991 to Lucero et al.

In view of what the prior art has previously proposed, it is clear that there exists a significant need for a penetrometer which incorporates numerous features in order to provide a host of data necessary for proper soil analysis. In addition, the need for a penetrometer which eliminates various parameters as variables is required in order to simplify collected data in order to provide an accurate soil representativeness determination. The present invention is directed to satiating these needs.

SUMMARY OF THE INVENTION

One object of the present invention is to provide an improved soil penetrometer and method of employing this penetrometer.

A further object of the present invention is to provide a portable soil penetrometer, comprising:
 frame means for supporting the penetrometer;
 a penetrometer probe having substrate penetrating means for penetrating a substrate, the penetrometer including means for applying an electromagnetic field in the substrate for detecting moisture therein;
 selectively controllable drive means for driving the penetrometer into the substrate under a constant force;
 detecting means for detecting force applied to the probe; and
 means for receiving data obtained by the probe.

Advantageously, one embodiment of the present invention provides for a portable lightweight soil penetrometer which is readily adapted for field use. To this end, the apparatus may include a lightweight power source, for example, a lightweight DC power source, a series of photo voltaic cells among a host of other lightweight power sources which will be readily apparent to those skilled in the art.

It has been found particularly useful to combine the feature of providing a constant non-variable applied force to the probe during an injection procedure within the substrate or soil together with means for emitting a signal and receiving a reflector signal in order to determine an in-situ water content. In the prior art, the marriage of these features was not proposed and accordingly, the prior arrangements were inherently limited in their utility for generating a representative indication of a soil sample in which the probe was placed. By eliminating the variable force application of the probe and the inability to detect soil moisture, a vast improvement has been realized particularly when the data generated is statistically more accurate and therefor more representative of the sample.

One form for the electromagnetic field may comprise radio frequency energy, however, it will be apparent that microwave energy, as well as any other form of energy on the electromagnetic spectrum can easily be employed for the determination of soil moisture.

The soil penetrometer apparatus may additionally be mounted to a vehicle, for example, a van or, depending on the soil conditions and the environment in which a sample is desired, it may be more practical to provide an unmanned remotely controlled vehicle for the apparatus.

A further object of the present invention is to provide a soil penetrometer probe, comprising:

an elongate body;

a soil penetrating tip releasably connected to the elongate body;

at least two electroconductive members connected to the body adapted for transmitting and receiving an electromagnetic signal in a substrate for detecting moisture content therein; and a signal applying means for applying a signal to the electroconductive members.

The penetrometer will include, in addition to the electroconductive members, a load cell or strain gauge which will connect the probe to the linear actuator for injecting the probe into the soil. The load cell is useful for compiling information with respect to the force realized by the probe.

Further, the probe tip is preferably releasably engageable with the elongate probe body. This feature permits a user to interchange probe tips from the conventional conical tip to, for example, a tip which would be more representative of an agricultural implement used in tillage etc. Other possibilities will be clear to those skilled in the art.

Regarding the elongate body, it is useful to employ a non-electroconductive material for the body in view of the fact that electroconductive members will be associated therewith. This prevents any extraneous signal or other interruption of the emission and reception of signals. Suitable materials can include, for example, composite materials, suitable plastics, etc. In addition, the cross-section of the elongate body may vary from a circular cross-section, for example, a polygonal cross-section, triangular, square, etc. The selected cross-section will depend on the type of soil into which the probe is injected and the revision for a variety of cross-sections may be useful where, for example, signal transmission from the probe would be enhanced by a non-circular cross-section.

A still further object of the present invention is to provide a method for in-situ determination of soil moisture in a soil sample comprising:

providing a soil penetrometer probe for injection into a sample of soils;

applying a constant non-variable force to the probe during injection into the soil;

emitting an electromagnetic signal from the probe into the soil;

receiving a return signal on the probe as a result of interaction of the signal with moisture; and determining moisture content in the soil.

By practising the method according to the present invention, numerous advantages can be realized, namely the ability to precisely control the rate of insertion and force acting on the penetrometer cone or tip and the addition of the electroconductive members to the probe which allows simultaneously measurements of both penetration resistance and water content on the same sample. It has been found that the apparatus and method according to the present invention provide for useful data which was not previously provided for in the prior art.

Having thus generally described the invention, reference will now be made to the accompanying drawings, illustrating preferred embodiments.

BRIEF DESCRIPTION OF THE DRAWINGS

FIG. 2 is a longitudinal cross-section of a probe employed with the present invention;

FIG. 3 is a sectional view along line 3—3 of FIG. 2;

DETAILED DESCRIPTION OF THE PREFERRED EMBODIMENTS

Figure 1:
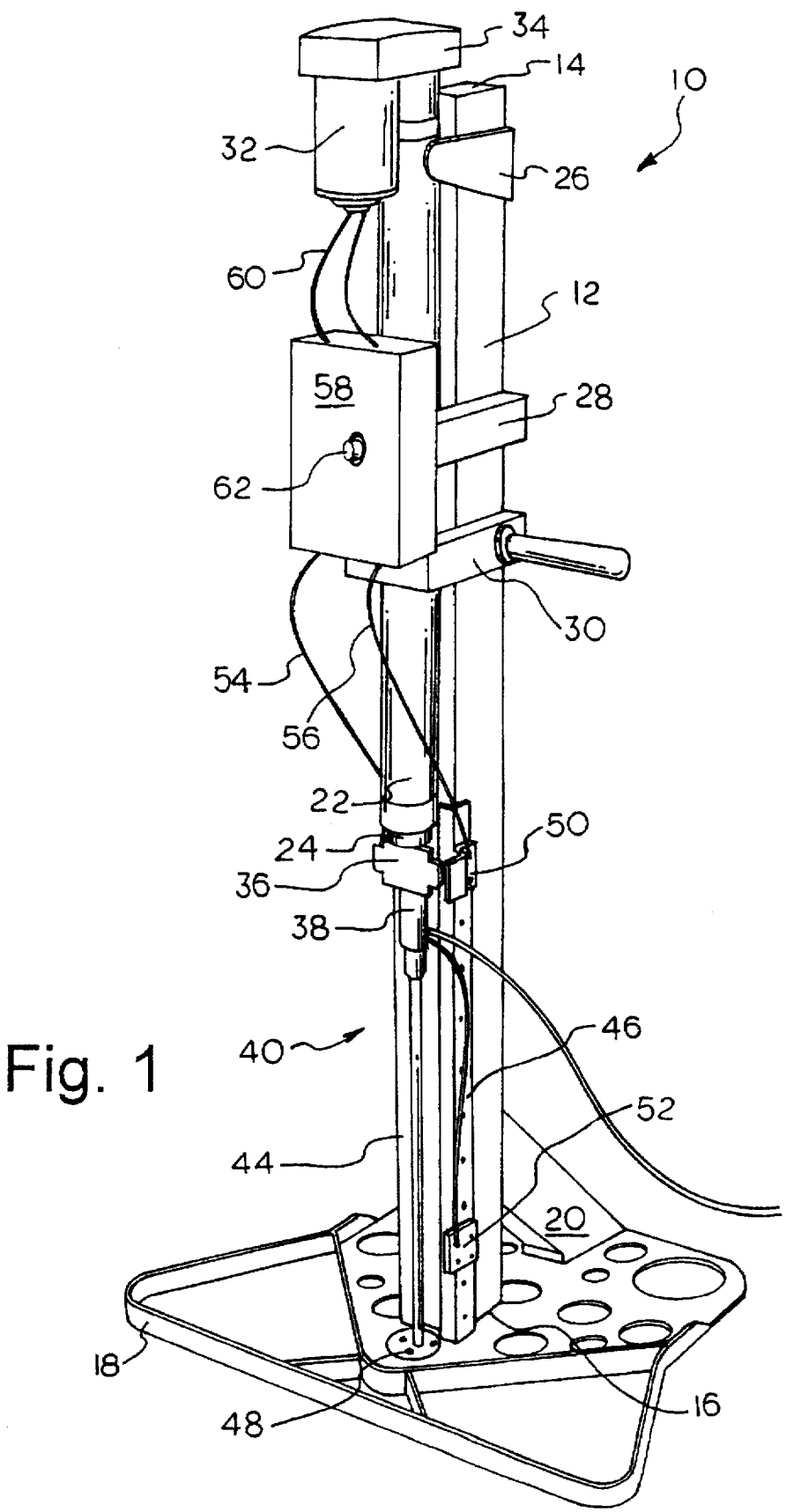
FIG. 1 is a perspective view of an embodiment of the present invention.

Referring now to the drawings, FIG. 1 is a perspective view of one embodiment of the present invention. The penetrometer apparatus, globally denoted by numeral 10 includes a vertical support member 12 having opposed ends 14 and 16, a base 18 being connected to opposed end 16 and a further stabilizing member 20 connected between support member 12 and base 18.

A selectively controllable injection or drive is provided in the form of a linear actuator having a cylinder 22 and internally disposed therein a movable, retractable piston 24. Mounting brackets 26, 28, 30 and cylinder 22 mount the linear actuator to the support member 12 at spaced-apart points on support member 12.

In order to effect actuation of piston 24, a motor 32 is provided to effect movement of a gear box 34, the gear box 34 being connected to the linear actuator and more specifically piston 24. A gear box 34 is of a conventional design readily apparent to those Skilled in the art. As a preferred arrangement, a DC motor 32 is employed due to the stability and smooth non-variable rotation that it imparts to the gears in gear box 34. This, of course, is an attractive feature since the constant force that is applied to the linear actuator is an important feature according to the present invention.

Piston 24 is connected to an intermediate member 36, which intermediate member movably mounts a strain transducer 38, the transducer 38 in turn, being connected to a penetrometer probe, broadly denoted by numeral 40 and discussed in greater detail hereinafter.

Figure 5:
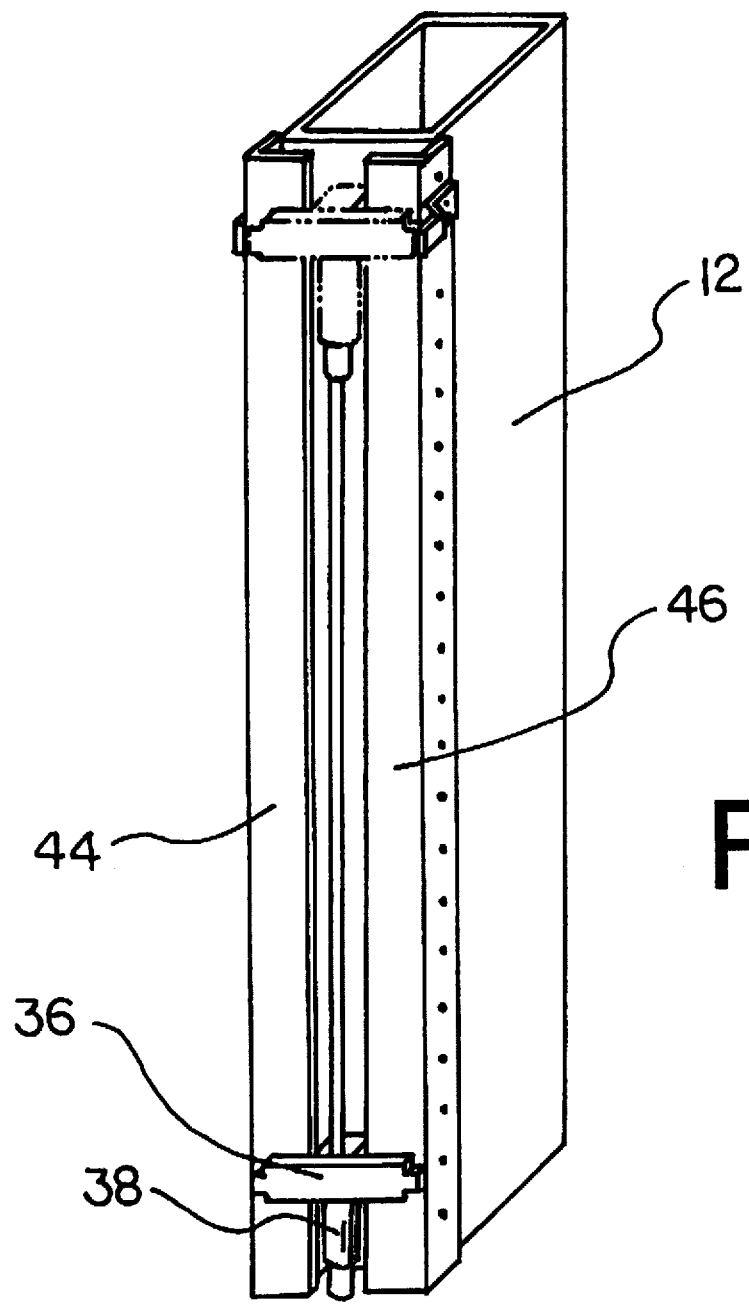
FIG. 5 is an isolated perspective view of the probe delivery system with parts removed for clarity.

Intermediate member 36 is configured to move within a channel 42, the intermediate member including, for example, a locator member 37 for movement therein. The channel 42 is defined by spaced-apart vertical guide members 44 and 46. These details are shown more clearly in FIG. 5. The guide members 44 and 46 and intermediate member 36 provide for smooth linear injection of the probe 40 into a sample to be sampled. To further assist in precise injection of the probe 40, a probe guide 48 is provided. In the example, the guide 48 is provided in the base 18, the guide 48 comprising a disc member with an aperture extending therethrough.

Switches 50 and 52 are provided on the apparatus 10 and are positioned in a spaced-apart relationship and more particularly, at the top and bottom of the probe. The switches are employed to indicate the position of the probe 40 and are used to deactivate the power source for motor 32 to thus stop the movement of the linear actuator and, therefore, the movement of the probe. Any suitable switch arrangements may be employed, examples of suitable arrangements include optical switches, mechanical switches, etc. As indicated briefly here and above, switches 50 and 52 include leads, broadly denoted by numerals 54 and 56, the leads extend into a control panel 58 mounted to frame 12. Control panel 58 houses the power source (not shown) for motor 32, the power being delivered by leads 60 as shown in the example. Operation of the linear actuator achieved by a master switch 62, shown in the example as a toggle switch. The user simply switches switch 62 to effect movement of the piston 24 for driving the probe 40 into a substrate or sample to be sampled. The cycle may be interrupted by simply turning the switch 62 to the off position.

Turning now to greater detail with respect to the probe 40, FIG. 2 shows a perspective view of one possible embodiment for the probe 40. As is known, the probe 40 includes a longitudinal rigid body 61 having opposed ends 63 and 64, end 63 threadably receiving a cone penetrometer head 66 as is known in the art. End 64 includes a strain transducer 38 as discussed briefly herein above. Transducer 38 includes a cable 68 which may comprise a coaxial cable.

Mounted to body 61 are a plurality of electroconductive members 70, 72, 74, and 76. FIG. 3 illustrates the disposition of the electroconductive members. As is illustrated, the members are in a spaced-apart relationship and, as shown in FIG. 2, the ends of the members are spaced from and out of contact with penetrometer head 66. Electroconductive members 72 through 76 are employed to measure soil water in a soil. This is done by time domain reflectrometry, a technique that increases the reliability of soil water content measurements. The use of time domain reflectrometry (hereinafter referred to as TDR) to measure soil water content has many advantages over previously proposed methods, including: the ability of TDR to provide high resolution and, the ability to measure close to the soil surface. This technique also offers rapid readings in the field with minimal soil disturbance.

Figure 4:
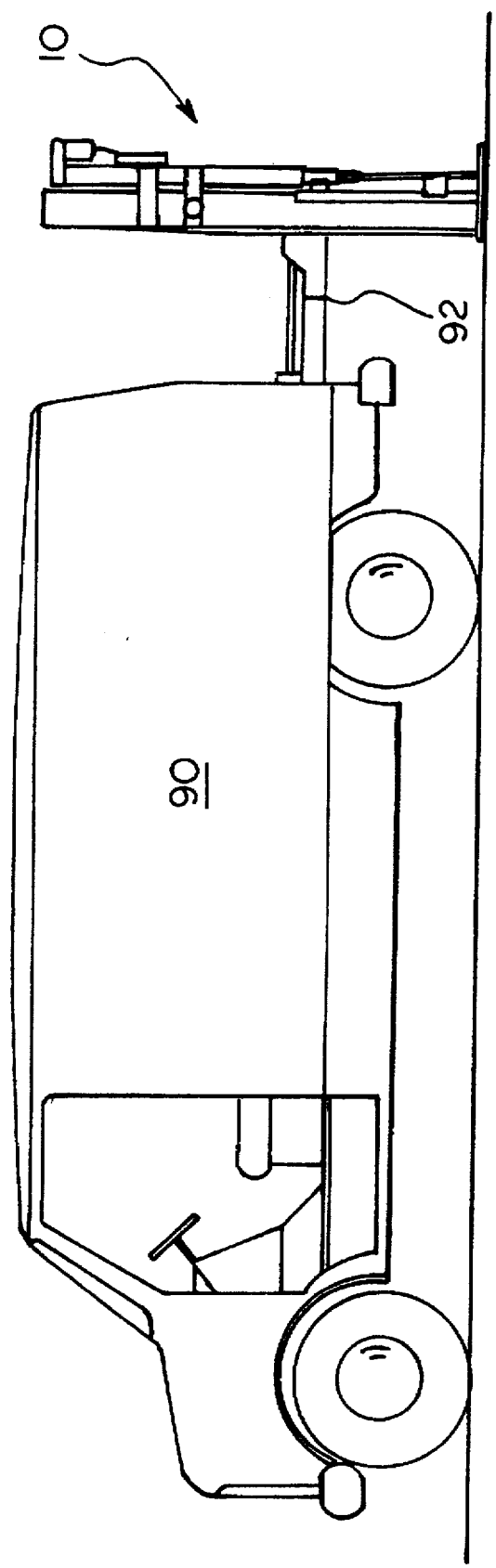
FIG. 4 is a further embodiment according to the present invention.

Referring now to FIG. 4, shown is a further embodiment according to the present invention. The soil penetrometer apparatus 10 may be mounted to a vehicle 90, e.g. van, all terrain vehicle, tractor etc., by suitable mounting members, shown in the example as a bracket 92. The bracket 92 may be pivotally connected (not shown) to the vehicle 90 and the apparatus 10 in order to facilitate ease in handling the apparatus 10. Other possibilities include a telescopic boom, hydromechanical arrangements etc.

The electroconductive members 70 through 76 act as transducers for transmitting a signal through, for example, soil when the probe 40 is injected into the soil and receives a reflected signal, the time of reflection being indicative of soil moisture content. The use of TDR for detecting soil moisture has been previously reported by Hook et al. in the article "Remote Diode Shorting Improves Measurement of Soil Water By Time Domain Reflectrometry", *Soil Science Society of America Journal*, Volume 56, September-October, 1992. As will be appreciated by those skilled in the art, any form of electromagnetic signal may be employed with the present apparatus. Suitable forms of electromagnetic radiation include, for example, microwave radiation, ultrasonic radiation, photoradiation, etc. Leads 68 will be connected to electroconductive members 70 through 76 as illustrated in FIG. 3, the leads being connected to a signal source (not shown).

By making use of the soil moisture TDR probe 40 together with the linear actuator, the latter providing for a constant non-variable force to be applied to the probe during an injection procedure, the result is a significantly improved soil penetrometer apparatus. By providing a constant force to the probe, the result is that the force no longer needs to be dealt with as a variable in the analysis of the data generated by the apparatus. If this force can be maintained as a constant, the same does not interfere with the generated data nor does it have any affect thereon. To further complement the apparatus, the ability to detect soil moisture on the probe using, for example, reflectrometry, the result is a significantly improved arrangement providing more accurate and more useful data to the soil scientist, researcher, engineer, or the military. As further possible embodiments, the power source may comprise solar cells or any other lightweight source of power. In addition, where the apparatus is to be employed in an environment where the substrate or soil has an irregular topography, the base may include telescopic legs in order to adjust the apparatus to the topography.

Although embodiments of the invention have been specifically disclosed herein, it will be appreciated by those skilled in the art that numerous modifications may be made without departing from the spirit, nature, and scope of the claimed invention.

I claim:

1. A portable soil penetrometer, comprising:

frame means for supporting said penetrometer;

a penetrometer probe having substrate penetrating means for penetrating a substrate, said penetrometer including means for applying an electromagnetic field in said substrate for detecting moisture therein;

selectively controllable drive means for driving said penetrometer into said substrate under a constant force;

detecting means for detecting force applied to said probe; and means for receiving data obtained by said probe.

2. The soil penetrometer as set forth in claim 1, wherein said selectively controllable drive means comprising a linear actuator, said linear actuator having a piston movable from a probe injecting position to a probe retrieving position.

3. The soil penetrometer as set forth in claim 2, wherein said linear actuator includes drive means for effecting movement of said piston, said drive means comprising low friction DC-powered drive means.

4. The soil penetrometer as set forth in claim 1, wherein said detecting means comprises a load cell .for detecting load experienced by said probe during injection into a substrate.

5. The soil penetrometer as set forth in claim 1, in combination with a vehicle, said vehicle including releasable engagement means for releasably engaging said frame means.

6. A soil penetrometer probe, comprising:

an elongate body for injection into a soil sample;

a soil penetrating cone tip releasably connected to said elongate body;

a plurality of electroconductive members in and spaced apart about said body for transmitting and receiving an electromagnetic signal in a substrate for detecting moisture content therein said electroconductive members in a spaced apart relationship with said cone tip; and a signal applying means for applying a signal to said electroconductive members.

7. The soil penetrometer probe as set forth in claim 6, wherein said probe including four electroconductive members in spaced apart relation about the periphery of said body.

8. A method for in-situ determination of soil moisture in a soil sample comprising:

providing a soil penetrometer probe for injection into a sample of soils;

providing selectively controllable drive means for applying a constant non-variable force to said probe during injection into said soil;

emitting an electromagnetic signal from said probe into said soil;

receiving a return signal on said probe as a result of interaction of said signal with moisture; and determining moisture content in said soil.

9. The in-situ determination of soil moisture as set forth in claim 8, further including the step of determining force experienced by said probe during injection.

10. The in-situ determination of soil moisture as set forth in claim 9, further including the step of compiling force data and signal data received from said probe.

\* \* \* \* \*